US00PP28288P3

(12) United States Plant Patent
Hanes

(10) Patent No.: US PP28,288 P3
(45) Date of Patent: Aug. 15, 2017

(54) ***PELARGONIUM* PLANT NAMED 'PEQZ0009'**

(50) Latin Name: ***Pelargonium* interspecific**
Varietal Denomination: PEQZ0009

(71) Applicant: SYNGENTA PARTICIPATIONS AG, Basel (CH)

(72) Inventor: Mitchell E. Hanes, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/999,622

(22) Filed: Jun. 6, 2016

(65) Prior Publication Data

US 2016/0366801 P1 Dec. 15, 2016

(51) Int. Cl.
*A01H 5/02* (2006.01)

(52) U.S. Cl.
USPC ..... Plt./324

(58) Field of Classification Search
USPC ..... Plt./324
See application file for complete search history.

*Primary Examiner* — Annette Para
(74) *Attorney, Agent, or Firm* — Dale Skalla

(57) ABSTRACT

A new *Pelargonium* plant named 'PEQZ0009' particularly distinguished by intense pink double flower inflorescences held above the green foliage, very heat and drought tolerant with continuous color through the medium extreme summer heat, and exceptional edema tolerance on a vigorous plant.

2 Drawing Sheets

Latin name of the genus and species of the plant claimed: *Pelargonium* interspecific.

Varietal denomination: 'PEQZ0009'.

BACKGROUND OF THE NEW PLANT

The present invention comprises a new *Pelargonium*, botanically known as *Pelargonium* interspecific and hereinafter referred to by the variety name 'PEQZ0009'.

'PEQZ0009' is a product of a planned breeding program. The new cultivar 'PEQZ0009' has intense pink double flower inflorescences held above the green foliage, very heat and drought tolerant with continuous color through the medium extreme summer heat, and exceptional edema tolerance on a vigorous plant.

'PEQZ0009' originates from a hybridization in a controlled breeding program made in February 2008 in a greenhouse in Guatemala. The female parent was an unpatented, proprietary plant of P. interspecific parentage, identified as '10518-4' a hot pink single flowered selection with a more trailing plant habit when compared to 'PEQZ0009'.

The male parent of 'PEQZ0009' was an unpatented, proprietary plant of P. interspecific parentage identified as '10622-1' with more blue-rose color florets and a more open plant habit when compared to 'PEQZ0009'. The resultant seed was sown in February 2009.

'PEQZ0009' was selected as one flowering plant within the progeny of the stated cross in May 2009 in a greenhouse in Gilroy, Calif.

The first act of asexual reproduction of 'PEQZ0009' was accomplished when vegetative cuttings were propagated from the initial selection in June 2009 in a greenhouse in Gilroy, Calif.

BRIEF SUMMARY OF INVENTION

Horticultural examination of plants grown from cuttings of the plant initiated in Jun. 2, 2016 in Gilroy, Calif., and continuing thereafter, has demonstrated that the combination of characteristics as herein disclosed for 'PEQZ0009' are firmly fixed and are retained through successive generations of asexual reproduction.

'PEQZ0009' has not been observed under all possible environmental conditions. The phenotype may vary significantly with variations in environment such as temperature, light intensity, and day length.

A Plant Breeder's Right for this cultivar was applied for in the European Union on Jun. 10, 2015, No. 2015/1215. 'PEQZ0009' has not been made publicly available more than one year prior to the filing of this application.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0009' with colors being as true as possible with an illustration of this type.

Figure 1:
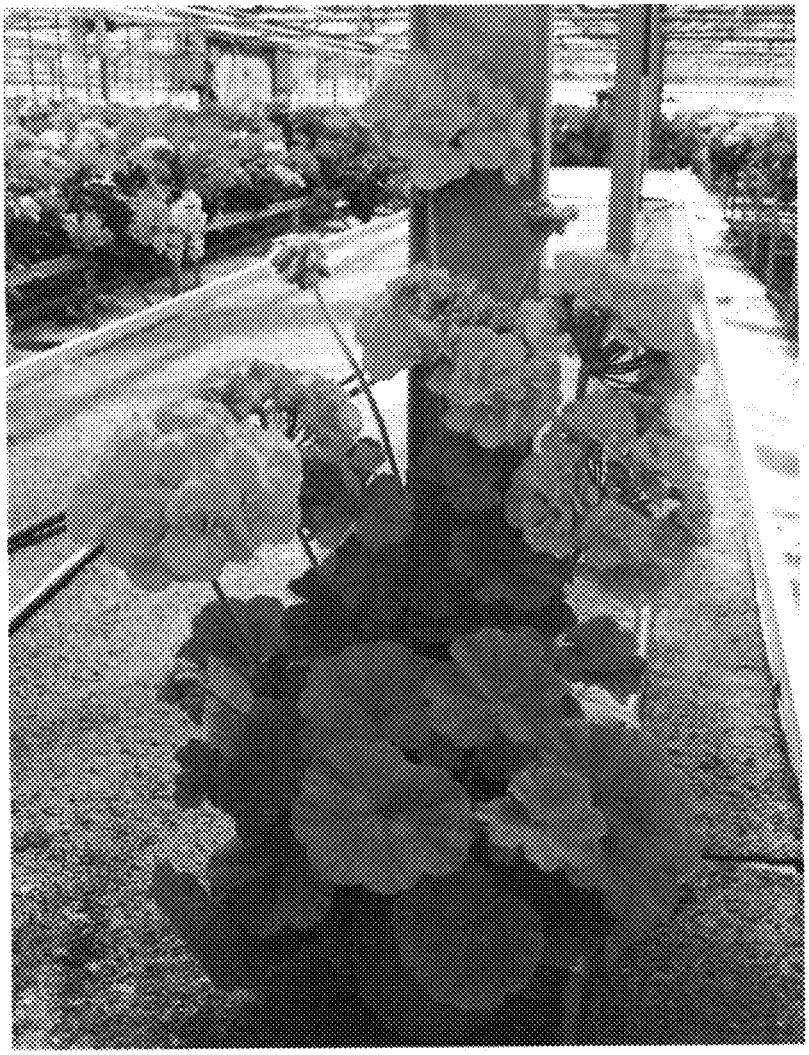
Figure 2:
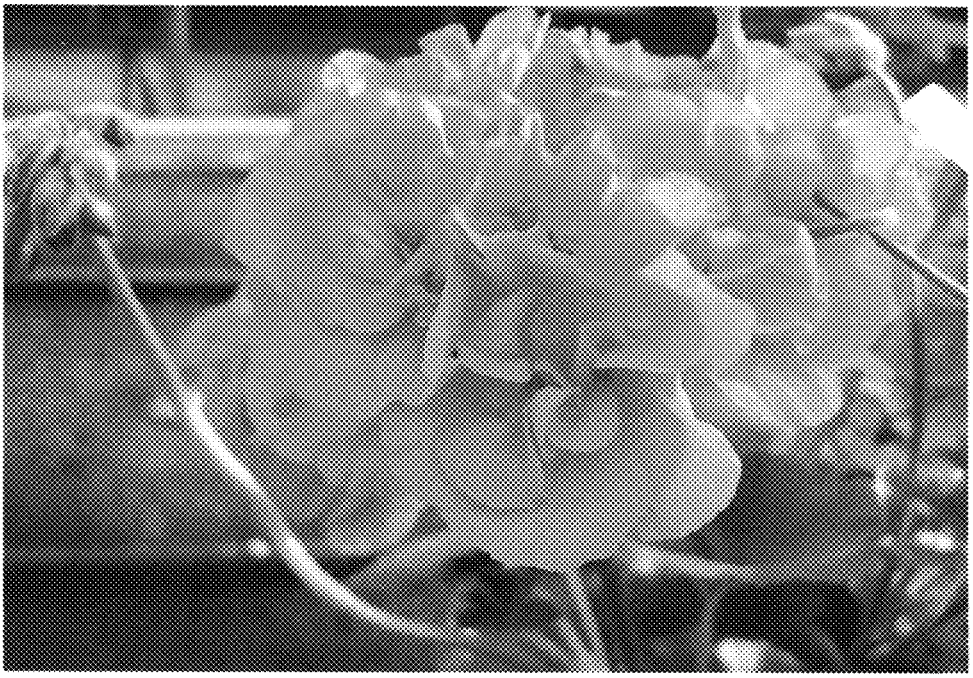

The photographic drawings show in FIG. 1, 3 flowering plants of the new variety and in FIG. 2, a close-up of an inflorescence.

DETAILED BOTANICAL DESCRIPTION

The plant descriptions and measurements were taken in Gilroy, Calif. in Jun. 2, 2016 under natural light. These plants were approximately 18 weeks old and were grown in a 4.5 inch pot, in a greenhouse trial.

Color references are made to The Royal Horticultural Society Colour Chart (R.H.S.) 2001.

Plant:

*Form, growth and habit.*—Upright, outwardly spreading and rounded growth habit, heat and drought tolerant with continuous color through the most extreme summer heat, edema tolerance, well-branched plant habit.

*Plant height.*—7.5-8.5 cm.

*Plant height (inflorescence included).*—23.5-25.5 cm.

*Plant width.*—23-24 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS 137A.

Foliage:

*Immature leaf, color upper surface.*—RHS 137B with a slightly lighter mottling.

*Immature leaf, lower surface.*—RHS 137C.

*Mature leaf, color upper surface.*—RHS 137B with slightly lighter mottling.

*Mature leaf, color lower surface.*—RHS 137C.

*Length.*—4.3-4.6 cm.

*Width.*—7.5-7.9 cm.

*Shape.*—Cordate.

*Base shape.*—Cordate.

*Apex shape.*—Acute.

*Margin.*—Slightly dentate.

*Texture upper side.*—Hirsute.

*Texture lower side.*—Hirsute.

*Leaf zonation color.*—None.

*Color of veins, upper surface.*—RHS 137B becoming indistinct.

*Color of veins, lower surface.*—RHS 137C becoming indistinct.

*Pattern of veining.*—Palmate.

*Petiole color.*—RHS 137C.

*Petiole length.*—6-9.0 cm.

*Diameter of petiole.*—0.2 cm.

*Texture.*—Pilose, hirsute, glandular hairs.

Stem:

*Quantity of branches.*—6-7.

*Color of stem.*—RHS 137C.

*Length of stem.*—4.4-4.8 cm.

*Diameter.*—0.7 cm.

*Length of internodes.*—1.4 cm.

*Texture.*—Sparsely hirsute, pilose, glandular hairs.

Peduncle:

*Color of peduncle.*—RHS 137C.

*Length of peduncle.*—13-15.0 cm.

*Peduncle diameter.*—0.3-0.35 cm.

*Texture.*—Hirsute, glandular hairs.

Pedicel:

*Color of pedicel.*—RHS 71A.

*Length of pedicel.*—5.5-6.8 cm.

*Diameter of pedicel.*—0.2 cm.

*Texture.*—Sparsely pilose, glandular hiars.

Bud (just before opening):

*Color.*—RHS 68B.

*Length.*—2.0 cm.

*Width.*—0.8-0.9 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—12, with 15 immature umbels in various stages.

*Fragrance.*—None.

*Umbel diameter.*—9.5-11.0 cm.

*Umbel depth.*—4.4-5.0 cm.

Corolla:

*Form.*—Double.

*Number of petals.*—8-10.

*Diameter of flower.*—3.9-4.2 cm.

*Depth of flower.*—1.6-1.8 cm.

*Color upper petals, upper surface.*—Between RHS N66B and RHS N66C.

*Color upper petals, lower surface.*—Closest to RHS N66D.

*Length of upper petals.*—2.2-2.3 cm.

*Width of upper petals.*—2.1-2.2 cm.

*Color lower petals, upper surface.*—RHS N66B.

*Color lower petals, lower surface.*—RHS 68A.

*Length of lower petals.*—2.2 cm.

*Width of lower petals.*—2.1 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS N144C.

*Length of sepals.*—0.9 cm.

*Width of sepals.*—0.3 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—1.0 cm.

*Style color.*—RHS 62D.

*Style length.*—0.8 cm.

*Stigma color.*—RHS 52C.

*Ovary color.*—RHS 142E.

*Ovary length.*—0.6 cm.

*Ovary diameter.*—0.2 cm.

Androecium:

*Number of stamens.*—5-7.

*Color of filaments.*—RHS N57B with RHS N155C basally.

*Length filaments.*—0.7 cm.

*Anther color.*—RHS 58C.

*Length of anthers.*—0.2 cm.

*Color of pollen.*—RHS 60D.

*Pollen amount.*—Normal.

*Fertility/seed set.*—Has not been determined to date.

*Disease/pest resistance.*—Has not been determined to date.

What is claimed is:

1. A new and distinct variety of *Pelargonium* plant named 'PEQZ0009' substantially as illustrated and described herein.

* * * * *